(12) United States Patent
Biedermann et al.

(10) Patent No.: US 12,076,057 B2
(45) Date of Patent: Sep. 3, 2024

(54) CONNECTION DEVICE FOR USE WITH EXTENSION MEMBERS OF A BONE ANCHOR

(71) Applicant: BIEDERMANN TECHNOLOGIES GMBH & CO. KG, Donaueschingen (DE)

(72) Inventors: Timo Biedermann, Trossingen (DE); Dimosthenis Dandanopoulos, VS-Schwenningen (DE)

(73) Assignee: BIEDERMANN TECHNOLOGIES GMBH & CO. KG, Donaueschingen (DE)

( * ) Notice: Subject to any disclaimer, the term of this patent is extended or adjusted under 35 U.S.C. 154(b) by 0 days.

(21) Appl. No.: 17/539,756

(22) Filed: Dec. 1, 2021

(65) Prior Publication Data
US 2022/0168024 A1    Jun. 2, 2022

Related U.S. Application Data

(60) Provisional application No. 63/120,413, filed on Dec. 2, 2020.

(30) Foreign Application Priority Data

Dec. 2, 2020 (EP) .................................. 20211362

(51) Int. Cl.
*A61B 17/70* (2006.01)
(52) U.S. Cl.
CPC ............................ *A61B 17/7076* (2013.01)
(58) Field of Classification Search
CPC .............. A61B 17/708; A61B 17/7077; A61B 17/7079
See application file for complete search history.

(56) References Cited

U.S. PATENT DOCUMENTS 9,289,250 B2    3/2016 Wall et al.
9,492,209 B2 *  11/2016 Biedermann ...... A61B 17/7032
                                                      606/265
(Continued)

FOREIGN PATENT DOCUMENTS

EP    2 957 246 A1    12/2015
EP    3 005 961 A1     4/2016
(Continued)

OTHER PUBLICATIONS

European Search Report for Application No. 20211362.7 mailed Jun. 9, 2021, 9 pages.

*Primary Examiner* — Ellen C Hammond
*Assistant Examiner* — Holly Joanna Lane
(74) *Attorney, Agent, or Firm* — Lewis Roca Rothgerber Christie LLP (57) ABSTRACT

A connection device includes a sleeve having a first end, a second end above the first end, a longitudinal axis, and a wall that extends at least partially around the longitudinal axis. An extension member of a bone anchoring device is insertable through the first end into the sleeve to position the sleeve around at least part of the extension member. The wall has an outer surface and defines a laterally extending opening. A surface at a lower end of the opening extends inwardly from the outer surface by a first distance to facilitate insertion of a free end of the extension member from the first end into the opening, while a surface at an upper end of the opening extends inwardly from the outer surface by a distance greater than the first distance to restrict the free end from extending past the upper end of the opening.

25 Claims, 7 Drawing Sheets

(56) References Cited

U.S. PATENT DOCUMENTS

| | | |
|---|---|---|
| 10,682,130 B2 | 6/2020 | White et al. |
| 10,959,859 B2 * | 3/2021 | Italiaie ............... A61B 17/7037 |
| 10,980,573 B2 * | 4/2021 | Su ...................... A61B 17/7076 |
| 2008/0077135 A1 * | 3/2008 | Stad ................... A61B 17/7076 |
| | | 606/68 |
| 2009/0099605 A1 * | 4/2009 | Fallin .................... A61B 90/06 |
| | | 606/252 |
| 2013/0096635 A1 * | 4/2013 | Wall ...................... A61B 90/92 |
| | | 606/305 |
| 2015/0066084 A1 * | 3/2015 | Petit .................... A61B 17/708 |
| | | 606/246 |
| 2015/0088210 A1 * | 3/2015 | Reitblat ............. A61B 17/7076 |
| | | 606/86 A |
| 2015/0164569 A1 | 6/2015 | Reitblat et al. |
| 2016/0095635 A1 * | 4/2016 | Gnoth ................ A61B 17/7091 |
| | | 606/266 |
| 2016/0331420 A1 * | 11/2016 | Dandanopoulos ... A61B 17/708 |
| | | 606/86 A |
| 2017/0079696 A1 * | 3/2017 | Walker ................. A61B 17/708 |
| | | 606/86 A |
| 2018/0353213 A1 | 12/2018 | Biedermann et al. |

FOREIGN PATENT DOCUMENTS

| | | |
|---|---|---|
| WO | WO 2011/127065 A1 | 10/2011 |
| WO | WO 2011/133160 A1 | 10/2011 |
| WO | WO 2020/214205 A1 | 10/2020 |
| WO | WO 2020/219018 A1 | 10/2020 |

* cited by examiner

CONNECTION DEVICE FOR USE WITH EXTENSION MEMBERS OF A BONE ANCHOR

CROSS-REFERENCE TO RELATED APPLICATION(S)

The present application claims priority to and the benefit of U.S. Provisional Patent Application No. 63/120,413, filed Dec. 2, 2020, the contents of which are hereby incorporated by reference in their entirety, and claims priority from European Patent Application EP 20 211 362.7, filed Dec. 2, 2020, the contents of which are hereby incorporated by reference in their entirety.

BACKGROUND

Field

The application relates to a connection device for use with extension members of a bone anchor, and to a system including such a connection device and a bone anchor. The connection device and the system are particularly applicable in spinal surgery.

Description of Related Art

Bone anchors used in particular in spinal surgery include a shank to be anchored in a bone and a receiving part with two free legs to receive a spinal rod therebetween. In minimally invasive surgery (MIS) only small incisions are made in the skin of a patient. To provide access to the bone anchor, extension members are used that extend the legs of the bone anchor to permit guiding and/or supplying elements of an implant or instruments to the bone anchor. US 2018/0353213 A1, for example, describes such a bone anchor with extension members.

In some cases, the extension members can be compressed towards each other in a direction transverse to their longitudinal axes of extension. This may result in a narrowing of the pathway to the bone anchor, which may cause difficulties when advancing instruments or elements to the bone anchor. In other cases, the extension members may be spread inadvertently and break off prematurely.

U.S. Pat. No. 9,289,250 B2 describes a collar for extenders, which is configured to receive the extenders and to maintain the extenders in a parallel orientation to prevent splaying and premature break-off.

SUMMARY

It is an object of the invention to provide an improved connection device for use with extension members of a bone anchor, and a system including such a connection device and the bone anchor which is simpler to handle.

According to an aspect, a connection device for use with extension members of a bone anchor includes a sleeve defining a longitudinal axis and configured to be placed at least partially around a portion of at least one of the extension members. The extension member has a free end and the sleeve includes a wall portion that is configured to extend at least partially around the extension member. The wall portion defines at least one opening that is configured to permit the free end of the extension member to extend at least partially therethrough.

According to another aspect, the connection device for use with extension members of a bone anchoring device includes a sleeve defining a longitudinal axis and configured to be placed at least partially around a portion of at least one of the extension members. The extension member has a free end and the sleeve has a contact surface configured to be contacted by at least one of the extension members. The contact surface is shaped and oriented such that when the sleeve is placed around the extension member and moved towards the bone anchor, a clamping force is generated which at least temporarily maintains or keeps the sleeve on the extension member.

In an embodiment, the contact surface of the sleeve and a cooperating surface of the extension member are inclined, such that an increasing clamping force is generated when the sleeve is mounted on the extension members.

The extension members preferably include a pair of extension members that are open at their free ends, i.e., are separated from each other at least in the region of their free ends, and more particularly are separated from each other along substantially their entire lengths. Such open extension members may have advantages, in particular in MIS, compared to extension members that are closed at their upper end opposite to the bone anchor. Such an advantage may be, for example, improved visibility of the implantation site.

With the connection device according to embodiments of the invention, it is possible to keep the space between the extension members open, if necessary. Further, it is possible to remove the connection device if the connection device is no longer required.

Moreover, the connection device according to embodiments of the invention provides stability to the extension members. In particular, the connection device can prevent the compression of the extension members towards each other and spreading of the extension members away from each other, respectively. Moreover, the connection device may be easily connectable to and removable from the extension members. Also, the connection device has a small size and is robust. In particular the open structure of the sleeve may contribute to the small size of the connection device.

Since the sleeve has a hollow interior, further instruments can be received therein. For example, an auxiliary instrument in the form of a pin can extend therethrough and project out of the sleeve for facilitating orientation and/or centering of the sleeve relative to the extension members. Instead of an auxiliary instrument, instruments for manipulating the bone anchor or components of the bone anchor may be inserted through the sleeve and guided by the extension members to the implantation site.

Still further, the connection device may be implemented in various manners. For example, the connection device may be used in connection with the alignment of the receiving part of a polyaxial bone anchor, in connection with the insertion of a locking member or of the rod, or in connection with the insertion and removal of an adapter, for example, for injecting bone cement or another substance.

The connection device may be used together with all kinds of bone anchors that have extension members, such as polyaxial bone anchors which include a shank pivotably connected to the receiving part, or monoaxial bone anchors which include a shank fixedly connected to a receiving part.

BRIEF DESCRIPTION OF THE DRAWINGS

Further features and advantages of the invention will become apparent from the description of embodiments by means of the accompanying drawings. In the drawings.

DETAILED DESCRIPTION

Figures 1, 2:
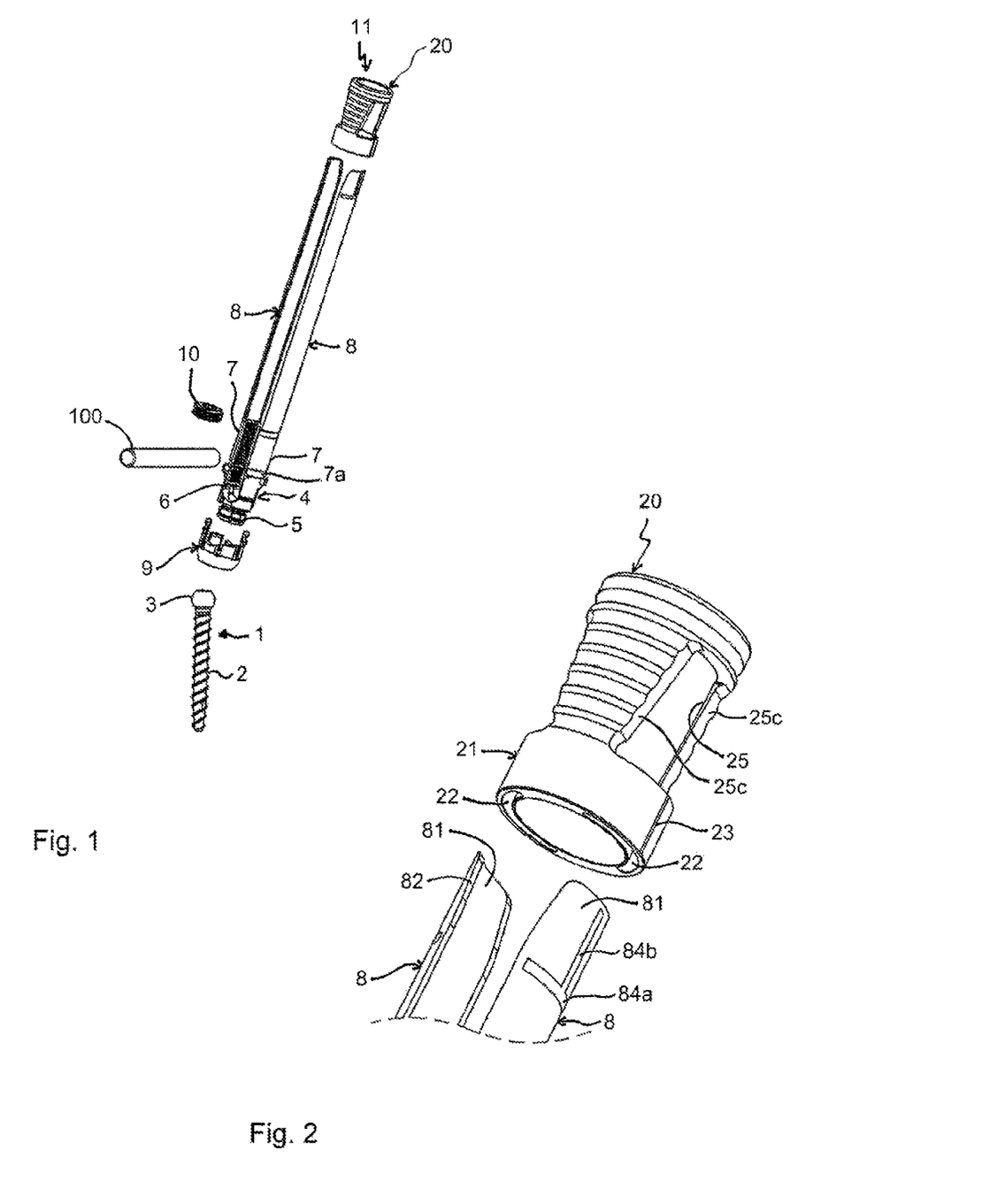
FIG. 1 shows a perspective exploded view of an embodiment of a connection device together with a bone anchor with extension members and a rod.
FIG. 2 shows a close-up of the perspective exploded view of end portions of the extension members of FIG. 1 with the connection device.
Figure 3:
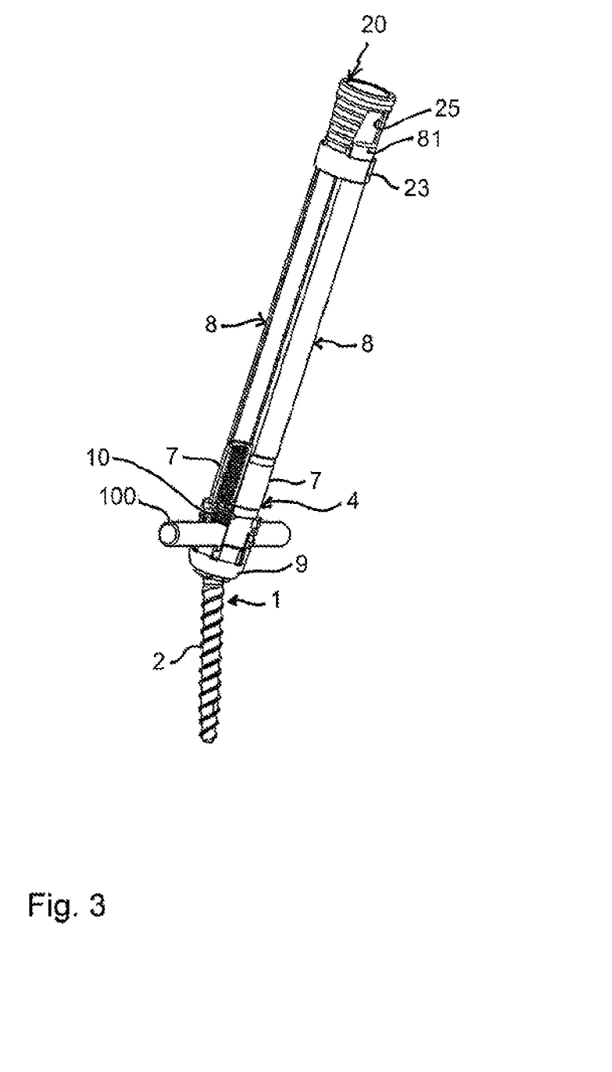
FIG. 3 shows a perspective view of the bone anchor with the extension members of FIGS. 1 and 2 and the connection device mounted on the extension members.
Figure 12:
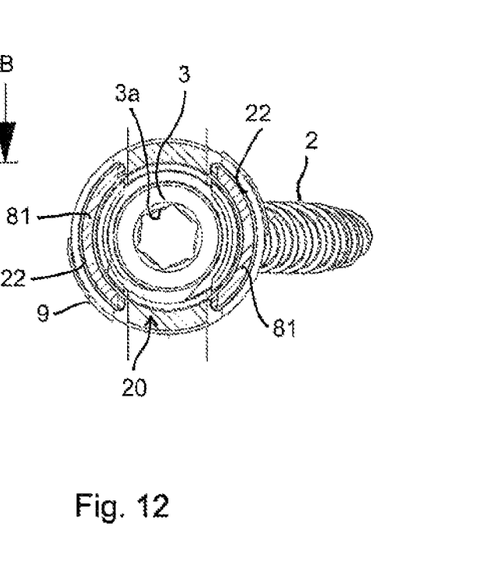
FIG. 12 shows a cross-sectional view of the bone anchor and the sleeve of the connection device of FIGS. 1 to 3, the cross-section taken along line B-B in FIG. 11.

Referring to FIGS. 1 to 3, a connection device is shown together with a polyaxial bone anchor. The polyaxial bone anchor includes an anchoring element 1 having a shank 2 with a bone engagement structure, such as a thread, and a head 3. The head may have a recess 3a for an instrument (see FIG. 12). A receiving part 4 with a head receiving portion 5 is configured to receive the head 3 in a pivotable manner. The receiving part 4 also includes a rod receiving portion including a substantially U-shaped recess 6, by means of which two upstanding legs 7 are formed. The recess 6 is configured to receive a rod 100 therein. In the embodiment shown, the legs 7 extend in an axial direction and may have a circumferentially extending weakened portion 7a for permitting an upper portion of the legs 7 to be broken off. Elongate extension members 8 are connected to the legs 7 that form extensions of the legs 7. A locking ring 9 is configured to extend around the head receiving portion 5 and to compress the head receiving portion to lock the head 3 at a particular angular position of the shank 2 relative to the receiving part 4. Between the legs 7, a locking member 10 can be inserted for locking the rod 100 in the recess 6, as shown in FIG. 3.

A connection device 11 is provided that is configured to be connected to each of the two extension members 8. By means of this, the extension members 8 can be connected with each other through the connection device 11, and can maintain a defined distance relative to each other along substantially their entire lengths. The connection device 11 includes a sleeve 20, and may optionally include an auxiliary member 30, as depicted in FIGS. 14a to 14e.

Figure 4:
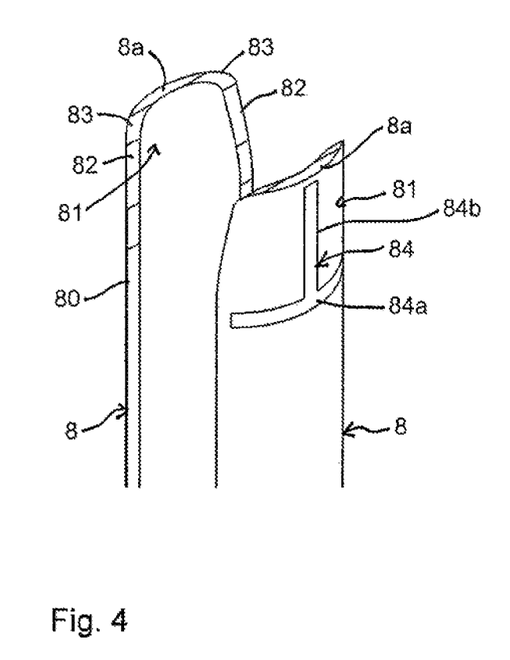
FIG. 4 shows a perspective view from a top of the end portions of the extension members of FIGS. 1 to 3.
Figure 5:
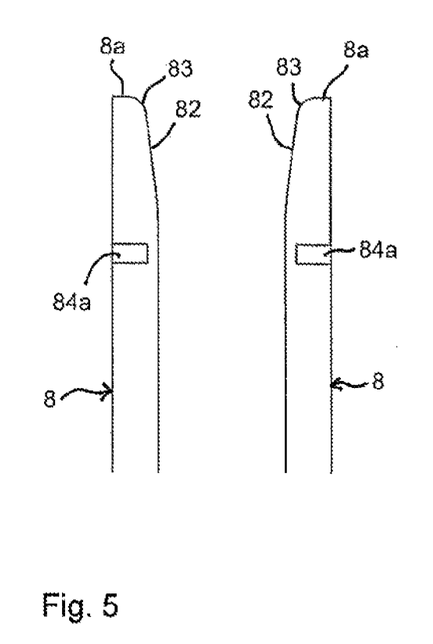
FIG. 5 shows a side-view of the end portions of the extension members of FIG. 4.
Figure 6:
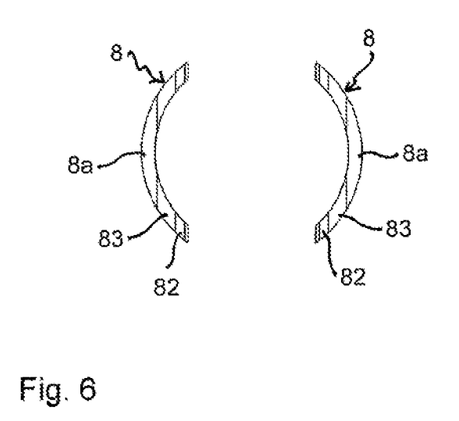
FIG. 6 shows a top view of the end portions of the extension members shown in FIGS. 4 and 5.
Figure 7:
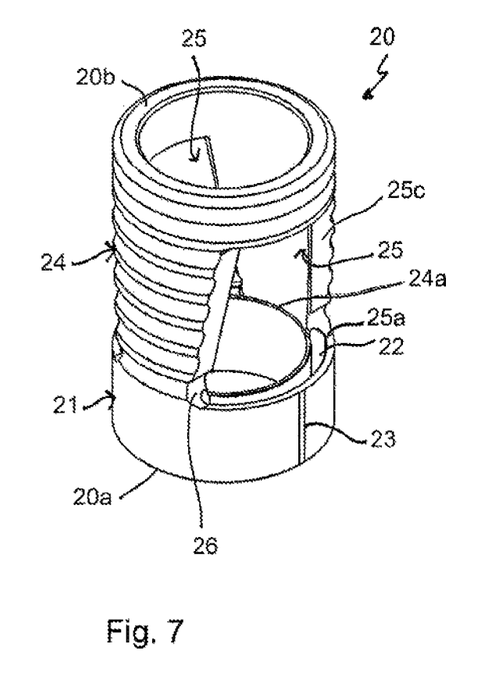
FIG. 7 shows a perspective view from a top of a sleeve of the connection device of FIGS. 1 to 3.
Figure 8:
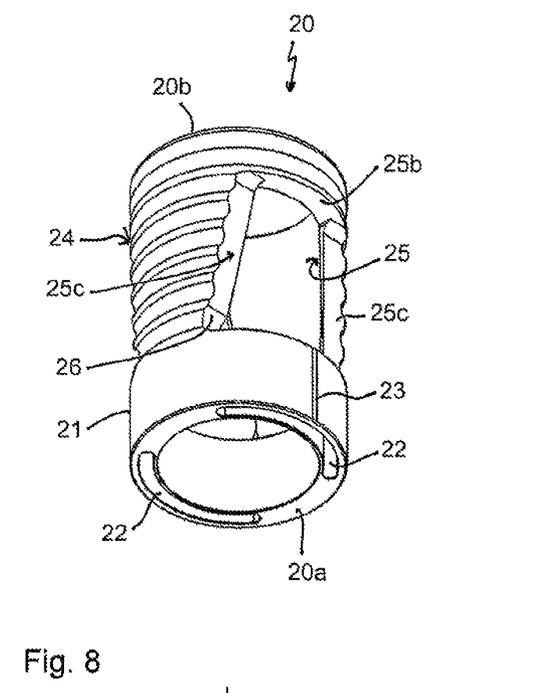
FIG. 8 shows a perspective view from a bottom of the sleeve of FIG. 7.
Figure 9:
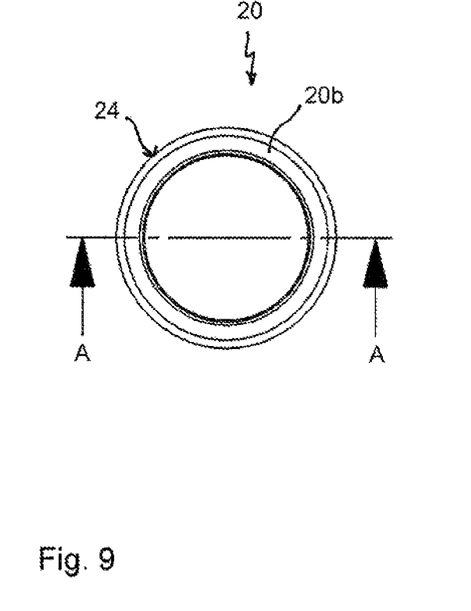
FIG. 9 shows a top view of the sleeve of FIGS. 7 and 8.
Figure 10:
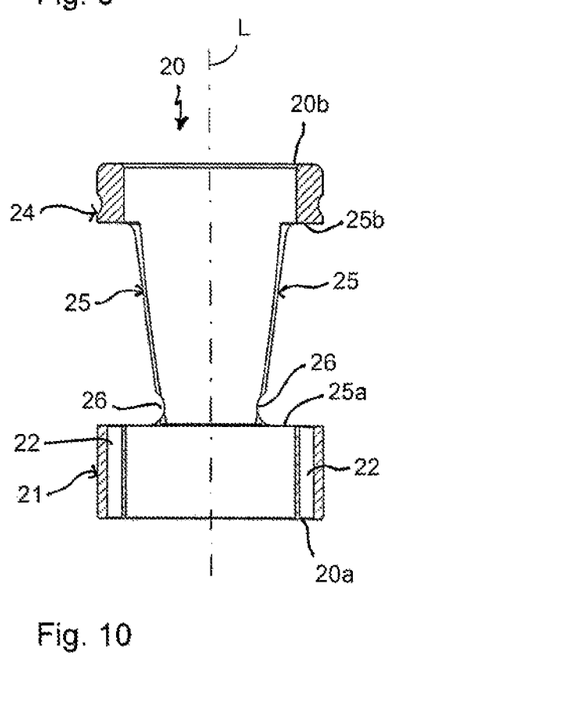
FIG. 10 shows a cross-sectional view of the sleeve of FIGS. 7 to 9, the cross-section taken along line A-A in FIG. 9.

Referring now in addition to FIGS. 4 to 6, the extension members 8 will be described in greater detail. The extension members 8 may have a substantially hollow cylinder segment shape, with an outer edge 80 and a free end 8a, where the cylindrical shape defines an axial direction and a circumferential direction. The shape of the extension members 8 preferably matches a cylinder segment shape of the legs 7 of the receiving part 4. Specifically, the circumferential width of each of the extension members 8 may be substantially the same as that of the legs 7. Thus, the extension members 8 are spaced apart from each other at a distance such that the rod 100 can pass therethrough. An inner surface of the extension members 8 may be thread-free. This permits the locking member 10 and/or further components to be advanced more easily between the extension members 8 in a sliding or non-rotating manner. In a region of an end portion 81 adjacent to the free end 8a of each of the extension members 8, the outer edge 80 includes an inclined edge portion 82 at either side in the circumferential direction. The inclined edge portion 82 is substantially flat and configured to cooperate with a corresponding inclined surface on the sleeve 20, as described below. The direction of the inclination is such that, as best seen in FIG. 5, the lateral or horizontal distance between points lying on the inclined edge portion 82 of one extension member and corresponding points at the same axial position of the other extension member have a continuously increasing distance from each other in the axial direction towards the free end 8a. Edge portions 83 between the free end 8a and the inclined edge portion 82 may be rounded. By virtue of the inclined edge portion 82, the width of the extension members in the circumferential direction decreases towards the free end 8a.

On the outer surface of each of the extension members 8, a marking 84 may be provided that serves for correctly orienting the sleeve 20 relative to the extension members 8 prior to connecting the sleeve to the extension members. The marking 84 may have a circumferentially extending first portion 84a that may be located at a greater distance from the free end 8a in the axial direction than the end of inclined edge portion 82 closest to the bone anchor. At substantially the centers of the extension members 8 in the circumferential direction, the marking 84 may further have a second portion 84b that extends in the axial direction.

The length of the elongate extension members 8 may be such that the extension members protrude a sufficient distance out of the skin of a patient when the bone anchor has been implanted into a bone part or a vertebra. The extension members 8 may be fixedly connected to the legs 7, e.g., by welding. Alternatively, the extension members 8 may be monolithically formed with the receiving part 4 and may have a break-off section that facilitates the breaking off and removal of the extension members. Still further alternatively, the extension members 8 may be removably connected to the legs, e.g., by a plug-in, clip-on, or a similar connection.

Figure 13:
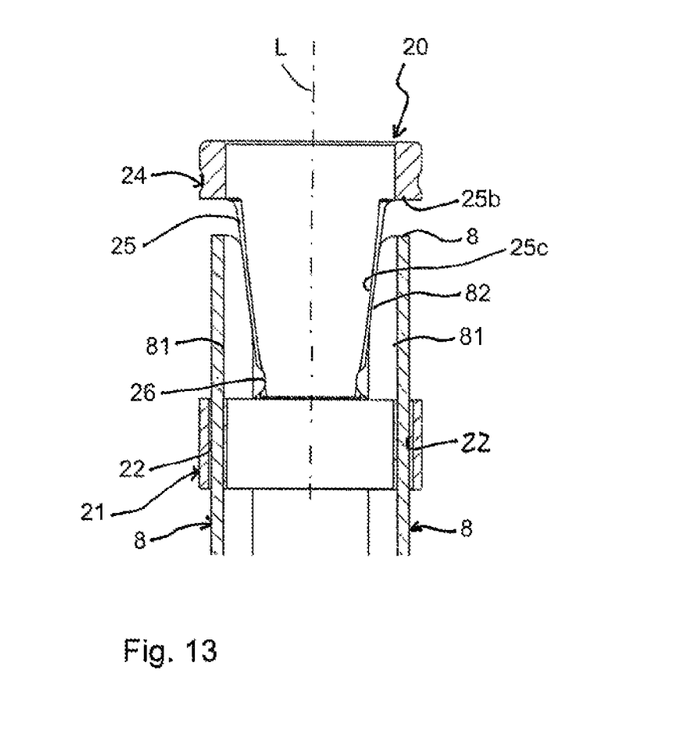
FIG. 13 shows a cross-sectional view of the end portions of the extension members with the sleeve mounted according to an embodiment of the invention, the cross-section taken in a plane including a central longitudinal axis of the sleeve and extending through centers of the extension members in the circumferential direction.

Referring additionally to FIGS. 7 to 13, the sleeve 20 will be described in greater detail. The sleeve 20 may be substantially cylindrical, and has a first end 20a and an opposite second end 20b. A cylinder axis of the sleeve defines a central longitudinal axis L. When the sleeve 20 is mounted to the extension members 8, the first end 20a faces towards the bone anchor. Adjacent to the first end 20a, a first portion 21 of the sleeve 20 may be a substantially cylindrical ring with a wall thickness that is greater than a thickness of the walls of the extension members 8 in a direction transverse to the longitudinal axis L. In the first portion 21, two opposite cylinder segment-shaped guiding recesses 22 are formed for guiding through at least the end portion 81 of the extension members 8, respectively. Hence, the inner contour of the guiding recesses 22 substantially matches the outer contour of the extension members 8 in a cross-section perpendicular to the longitudinal axis L. The guiding recesses 22 are offset by 180° from one another, so that each of the guiding recesses 22 can guide one extension member 8 therethrough. A height of the first portion 21 in the axial direction may be such that, when the inclined edge portion 82 of the extension member 8 has passed through the guiding recess 22, the first portion 84a of the marking is visible above the guiding recess 22 as illustrated, for example, as seen in FIG. 14e. Approximately at a position corresponding to the center of each guiding recess 22 in the circumferential direction, an axially extending marking 23 is provided on the outer surface of the first portion 21. The marking 23 serves to facilitate proper orienting of the sleeve 20 with respect to the extension members 8.

Figure 11:
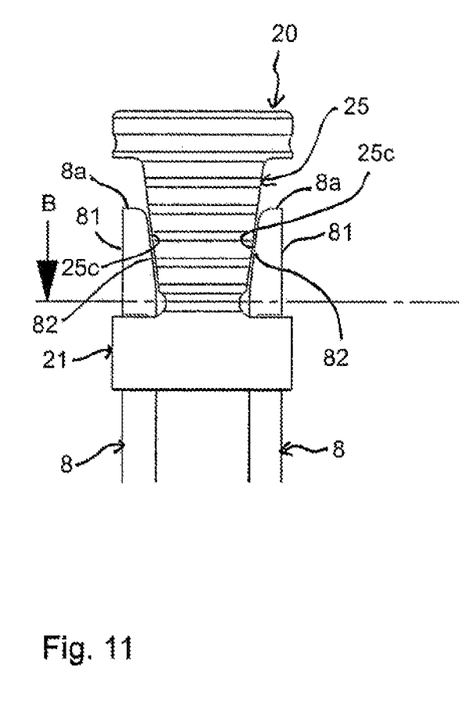
FIG. 11 shows a side-view of the end portions of the extension members with the sleeve mounted thereon according to an embodiment of the invention.

Between the second end 20b and the first portion 21, the sleeve has a second portion 24 which may also be cylindrical with a slightly greater inner diameter than the first portion 21. By means of this, a step 24a may be formed between the first portion 21 and the second portion 24. In the axial direction above the guiding recesses 22, two recesses 25 offset by 180° from one another are formed in the cylindrical surface of the second portion 24. The recesses 25 each has a base 25a that is provided by the upper edge of the first portion 21 and that has a width in the circumferential direction that substantially corresponds to or is slightly greater than the circumferential width of the guiding recesses 22. A top edge 25b of the recesses 25 also extends in the circumferential direction and is shorter than the base 25a. Hence, the circumferential width of the recesses 25 is smaller at the top edge 25b than at the base 25a, corresponding to the decreasing width of the end portions 81 of the extension members 8. The edges between the top edge 25b and the base 25a of the recesses 25, respectively, are formed as substantially flat inclined surfaces 25c that are oriented outwards. The size of the recesses 25 in the axial direction are such that the end portions 81 of the extension members 8 can extend therein to such an extent that the first marking 84a of the extension members 8 is visible within the recess 25 above the base 25a. At least part of the inclined surface 25c forms a contact surface that is configured to cooperate with the inclined edge portion 82 of the extension members 8, respectively. Hence, each recess 25 has two inclined surfaces 25c facing in the same outward direction. The inclination of the inclined surface 25c is such that points at the same axial height on the inclined surfaces of opposite recesses 25 have an increasing distance between them from the base 25a towards the top edge 25b. More specifically, the inclination of the inclined surface 25c is such that, when the end portion 81 of the extension member 8 enters the recess 25 but is not yet at an uppermost position, there is still a clearance between the inclined edge portion 82 and the inclined surface 25c, as depicted in FIG. 11. When the end portion 81 of the extension member 8 is further moved into the recess 25 and contacts the inclined surface 25c, as shown in FIG. 13, the friction force generated thereby increases and clamps the sleeve 20 on the extension members 8. The angle of inclination of the inclined surface 25c relative to the central longitudinal axis L may be, depending on the friction between the surfaces, between around 5° and 20°, and more preferably around 8° to 12°. Preferably the angle of inclination is greater than an angle that would produce a self-locking effect.

Although the extension member may not reach up to the upper edge 25a of the recess 25, the upper edge 25a may serve as a stop for limiting a downward movement of the sleeve when the sleeve 20 is mounted to the extension members 8. Between the inclined surfaces 25c and the base 25a, an additional recess or groove 26 may be formed on either end to provide more space when the end portion 81 of the extension member enters into the recess 25. An outer surface of the second portion 24 of the sleeve 20 may have a gripping structure for facilitating gripping, such as a plurality of circumferentially extending flutes or corrugations.

Referring now to FIGS. 14a to 14e, the auxiliary member 30 will be described in greater detail. The auxiliary member 30 includes a substantially cylindrical pin 31 with a bevelled front end portion 32. An outer diameter of the cylindrical pin 31 corresponds substantially to an inner diameter of the second portion 24 of the sleeve 20, so that the pin 31 can be inserted into the sleeve 20 and guided therein, and preferably can be held by friction therein. The length of the pin 31 is such that, in the inserted state, at least the bevelled front end portion 32 and preferably a still further portion of the pin 31 can protrude out of the first end 20a of the sleeve 20. At the side opposite to the bevelled front end portion 32, a head 33, for example a cylindrical head, is formed that has a greater diameter than the pin 31, so that a step 33a is formed at the transition. The step 33a functions as a stop for the insertion of the auxiliary member 30 into the sleeve 20.

The auxiliary member 30 serves for facilitating the connection of the sleeve 20 to the extension members 8. This may be achieved by the centering function of the bevelled front portion 32. In addition, the pin 31 is configured to keep the end portions 81 of the extension members at a distance such that the end portions can be aligned with the guiding recesses 22 and inserted therein.

The parts and portions of the bone anchor and of the connection device including the sleeve and the auxiliary member may be made of any material, preferably however, of titanium or stainless steel, or of any biocompatible metal or metal alloy or plastic material. For biocompatible alloys, a NiTi alloy, for example Nitinol, may be used. Other materials that can be used may include magnesium or magnesium alloys. Biocompatible plastic materials that can also be used may be, for example, polyether ether ketone (PEEK) or poly-L-lactide acid (PLLA). The parts can be made of the same or of different materials from one another.

In the clinical use, first, the bone anchor is inserted into bone or into a vertebra. For example, the bone anchor can be a polyaxial pedicle screw, the shank 2 of which is inserted into the pedicle of a vertebra. In a first way of use, the receiving part 4 is preassembled with the anchoring element 1. Then, the shank 2 is inserted into the bone or vertebra. In a second way of use, the shank 2 is first inserted into the bone or vertebra, and thereafter the receiving part 4 is mounted onto the head 3 of the anchoring element 1. In any case, the extension members 8 protrude from the skin of the patient.

The two extension members 8 are then connected by the sleeve 20. In a first way of use, the sleeve 20 is placed on the extension members without using the auxiliary member 30. In order to mount the sleeve 20 on the extension members 8 in the correct orientation, the marking 23 on the first portion 21 of the sleeve 20 is aligned with the second marking portion 84*b* of the extension members 8, respectively. The sleeve 20 is then slid onto the end portion 81 of the extension members 8, such that the end portions 81 pass through the guiding recesses 22, respectively, and enter the recesses 25, as shown in FIG. 11. When the inclined edge portions 82 of the extension members 8 and the inclined surfaces 25*c* of the sleeve 20 engage, as shown in FIG. 13, a friction force is generated that holds the sleeve 20 and the extension members 8 together. The complete visibility of the first marking portion 84*a* of the extension members 8 may be used as an indication that the sleeve 20 is substantially fixed to the extension members 8.

Figure 14A:
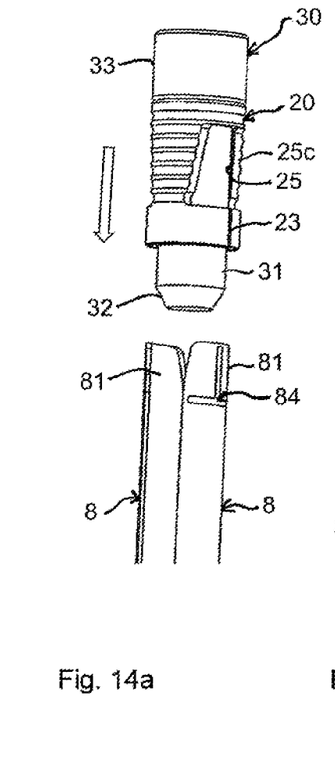
FIGS. 14a to 14e show steps of mounting the connection device with an inserted auxiliary member to the extension members of the bone anchor, and removal of the auxiliary member, according to an embodiment of the invention.
Figure 14B:
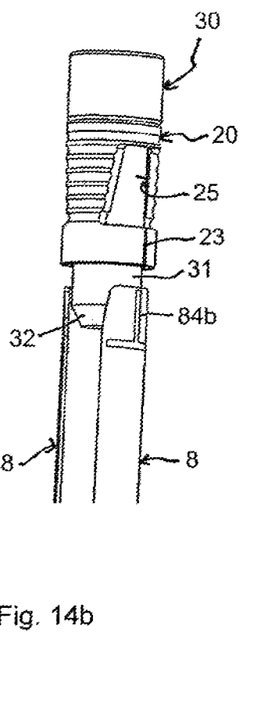
Figure 14C:
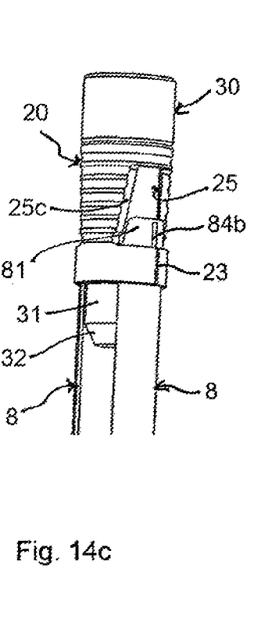
Figure 14D:
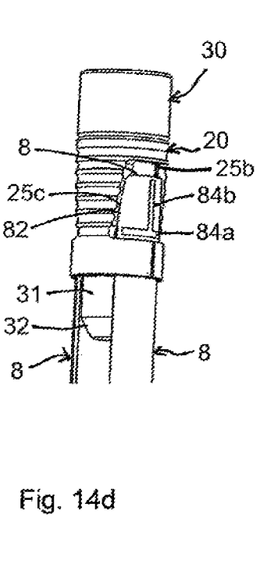
Figure 14E:
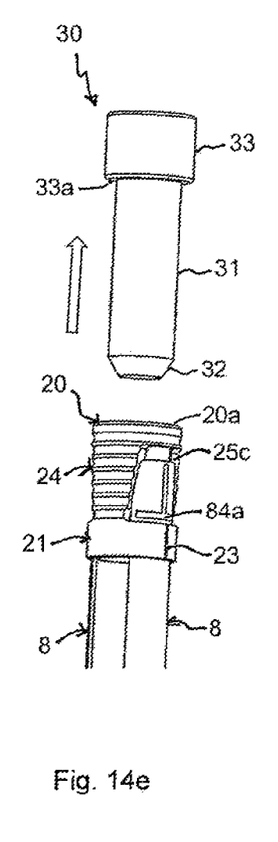

In a second manner of use, as shown in FIGS. 14*a* to 14*e*, the auxiliary member 30 is used for more easily placing the sleeve 20 on the extension members 8. First, the auxiliary member 30 is inserted with the pin portion 31 into the sleeve 20. Then, as shown in FIG. 14*a* the preassembled connection device including the sleeve 20 and the auxiliary member 30 is oriented with respect to the extension members 8 such that the marking 23 on the sleeve is aligned with the second marking portion 84*b* on the extension members 8. In FIG. 14*b*, the bevelled end portion 32 of the auxiliary member 30 and a portion of the pin 31 has entered the space between the extension members 8. The bevelled end portion 32 facilitates centering of the sleeve with respect to the extension members. The connection device is then further moved in the direction towards the bone anchor and can still be rotated until the markings 23 and 84*b* are exactly aligned.

As shown in FIG. 14*c* the end portions 81 of the extension members 8 have passed through the guiding recesses 22 until the free end 8*a* has entered the recess 25 of the sleeve. The inclined surfaces of the sleeve 20 and the extension members 8 then contact each other and a friction force is generated. As shown in FIG. 14*d*, the extension members 8 can be moved into the recesses 25 at least until the first marking 84*a* on the extension member is fully visible within the recess 25. The friction force is then sufficiently high to prevent sliding off of the sleeve from the extension members. Finally, as shown in FIG. 14*e*, the auxiliary member can be removed.

With the sleeve 20 placed onto the extension members 8, the extension members are prevented from being compressed towards each other and/or spread apart from each other. Hence, the extension members can maintain a substantially constant distance or parallel configuration with respect to each other.

Figure 15:
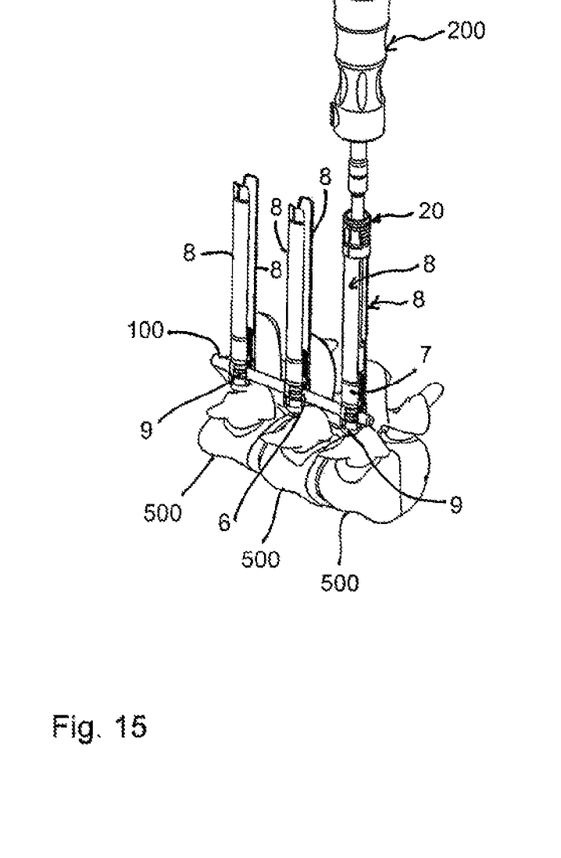
FIG. 15 shows a perspective view of a bone anchor with extension members and the sleeve of the connection device mounted thereon according to an embodiment of the invention, and an instrument extending through the sleeve and between the extension members.

As depicted in FIG. 15, usually a plurality of bone anchors has been inserted into bone, or in the specific example into the pedicles of adjacent vertebrae 500, and the rod 100 is inserted into the recesses 6 of the receiving parts 4 of the bone anchors. The sleeve 20 is connected to the extension members 8 of one of the bone anchors, and the locking member 10 can be inserted or manipulations can be made through the sleeve with an instrument 200. The sleeve 20 can then be removed and placed onto the neighboring extension members. Alternatively, each of the bone anchors may be provided with a separate sleeve. After the surgical steps have been completed, the extension members 8 and the portion of the legs 7 above the weakened portion 7*a* are broken off and removed.

Further modifications of the embodiment of the connection device are also possible. For example, it may be sufficient if one of the cooperating surfaces of the sleeve and the extension members is inclined, while the other one may be straight. The recesses 22 do not need to be closed towards the inside of the sleeve. It may be sufficient to provide only a lateral guidance for the extension members. Hence, the guiding recesses 22 may be at least partially or fully open towards the inside.

Also, it is possible to prevent falling off of the sleeve by other means, for example, by resilient engagement of detent portions in recesses or similar means.

The parts are also not limited to their detailed shape as depicted in the embodiments. The receiving part shown is only an example, and all receiving parts that are suitable for use with extension members can be used with the connection device. Also, the shape of the extension members may be different, and the guiding recesses and the cooperating surfaces at the sleeve may be adapted to such different shapes. For the anchoring element, all kinds of bone anchors, such as screws, nails, hooks, etc., either cannulated or non-cannulated, may be used.

While the present invention has been described in connection with certain exemplary embodiments, it is to be understood that the invention is not limited to the disclosed embodiments, but is instead intended to cover various modifications and equivalent arrangements included within the spirit and scope of the appended claims, and equivalents thereof.

What is claimed is:

1. A connection device for use with extension members of a bone anchoring device, the connection device comprising:
a sleeve having a first end, a second end above the first end, and a longitudinal axis that extends between the first and second ends, and comprising a wall between the first and second ends that extends at least partially around the longitudinal axis, wherein at least one of the extension members of the bone anchoring device is insertable through the first end into the sleeve to position the sleeve around at least part of the extension member;
wherein the wall has an outer surface and defines at least one opening that extends in a direction transverse to the longitudinal axis from the outer surface into the wall, and wherein a surface at a lower end of the opening extends inwardly in the direction transverse to the longitudinal axis from the outer surface by a first distance to facilitate insertion of the free end of the extension member from the first end into the opening, while a downwardly facing surface that defines an upper end of the opening extends inwardly in the direction transverse to the longitudinal axis from the outer surface into the wall by a second distance greater than the first distance to restrict the free end from extending axially past the upper end of the opening.

2. The connection device of claim 1, wherein a contact surface that extends axially between the upper and lower ends of the opening is configured to engage and exert a clamping force on the extension member to hold the sleeve at least temporarily on the extension member.

3. The connection device of claim 2, wherein the contact surface is inclined with respect to the longitudinal axis, such that a circumferential width of the opening at the lower end is greater than a circumferential width of the opening at the upper end.

4. The connection device of claim 1, wherein the sleeve defines two openings at opposite sides of the longitudinal axis for cooperating with two opposite extension members of the bone anchoring device.

5. The connection device of claim 1, wherein the sleeve further comprises a guiding surface for guiding the extension member.

6. The connection device of claim 5, wherein the guiding surface defines a recess that extends axially from the first end towards the second end and that is sized to receive a portion of the extension member.

7. The connection device of claim 6, wherein the recess is substantially closed on a side of the sleeve that faces the longitudinal axis in a radial direction.

8. The connection device of claim 1, wherein a stop is formed at the upper end of the opening for limiting an axial movement of the sleeve relative to the extension member.

9. The connection device of claim 1, wherein the sleeve further comprises a marking on the outer surface that facilitates alignment of the sleeve relative to the extension member.

10. The connection device of claim 1, further comprising an auxiliary member that is insertable through and removable from the sleeve.

11. The connection device of claim 10, wherein the auxiliary member comprises a stop for limiting an amount the auxiliary member is insertable through the sleeve.

12. The connection device of claim 1, wherein at least part of the sleeve forms a closed ring that extends completely around the longitudinal axis.

13. A system comprising:
a bone anchoring device comprising a shank for anchoring in bone, and a receiving part configured to be connected to the shank, wherein the receiving part comprises two sidewalls that define a channel therebetween for receiving a rod and at least one extension member that extends axially from one of the sidewalls; and
a connection device comprising a sleeve having a first end, a second end above the first end, and a longitudinal axis that extends between the first and second ends, and comprising a wall between the first and second ends that extends at least partially around the longitudinal axis, the wall having an outer surface and defining at least one opening that extends from the outer surface through the wall in a direction transverse to the longitudinal axis;
wherein the extension member of the bone anchoring device is insertable through the first end of the sleeve into a portion of the opening that extends through the wall to position the sleeve around at least part of the extension member, while a downwardly facing surface that extends inwardly in the direction transverse to the longitudinal axis from the outer surface through the wall defines an end of the opening farthest away from first end of the sleeve that is configured to directly engage a free end of the extension member to restrict the free end from extending axially past the end of the opening.

14. The system of claim 13, wherein the receiving part comprises two opposite extension members that extend axially from the two sidewalls, respectively, and wherein the sleeve is configured to extend around both of the extension members.

15. The system of claim 14, wherein at least part of the sleeve forms a closed ring that extends completely around the longitudinal axis.

16. The system of claim 14, wherein the connection device further comprises an auxiliary member that is insertable through and removable from the sleeve, and to be inserted between the extension members to facilitate positioning of the sleeve around the extension members.

17. The system of claim 14, wherein the extension members are movable towards and away from one another in a direction substantially perpendicular to the longitudinal axis.

18. The system of claim 13, wherein a contact surface on the sleeve that extends axially along a side of the portion of the opening that extends through the wall is configured to engage and exert a clamping force on the extension member when the extension member is inserted into the sleeve, to hold the sleeve at least temporarily on the extension member.

19. The system of claim 18, wherein the contact surface is inclined with respect to the longitudinal axis, to exert an increasing clamping force on the extension member as the extension member is inserted farther into the sleeve.

20. The system of claim 19, wherein the extension member comprises an inclined contact surface configured to engage the contact surface of the sleeve, such that the clamping force is a friction force that is generated between the respective contact surfaces.

21. The system of claim 13, wherein a circumferential width of at least part of the opening is wider than a circumferential width of the extension member.

22. A system comprising:
a bone anchoring device comprising a shank for anchoring in bone, and a receiving part configured to be connected to the shank, wherein the receiving part comprises two sidewalls and two extension members extending axially from the sidewalls, respectively, which define a channel therebetween for receiving a rod, the channel having an axial height extending from a base of the sidewalls to free ends of the extension members; and
a connection device comprising a sleeve having a first end, a second end above the first end, and a longitudinal axis that extends between the first and second ends, and comprising a wall between the first and second ends that extends at least partially around the longitudinal axis, the wall having an outer surface and defining two openings on opposite sides of the longitudinal axis that each extends from the outer surface through the wall in a direction transverse to the longitudinal axis, wherein a circumferential width of at least part of each of the openings is wider than a circumferential width of each of the extension members;
wherein the extension members are insertable through the first end of the sleeve into respective ones of the openings to position the sleeve around at least part of the extension member, and wherein for each of the openings, a downwardly facing surface that defines an upper end of the opening extends inwardly in the direction transverse to the longitudinal axis from the outer surface of the wall into the wall to directly engage the free end of the corresponding extension member to restrict the free end from extending axially past the upper end of the opening, while a majority of the axial height of the channel remains sufficiently unobstructed to facilitate insertion and axial movability of the rod in the channel.

23. The connection device of claim 1, wherein the downwardly facing surface that defines the upper end of the opening is configured to directly engage the free end of the extension member to restrict the free end from extending axially past the upper end of the opening.

24. The connection device of claim 1, wherein the surface at the lower end of the opening that extends inwardly from the outer surface is an upwardly facing surface.

25. The connection device of claim 1, wherein the free end of the extension member is insertable into a portion of the opening that extends from the outer surface into the wall.

* * * * *